United States Patent
Harrold et al.

(10) Patent No.: US 7,062,971 B2
(45) Date of Patent: Jun. 20, 2006

(54) MONITORING THERMAL BARRIER COATING DETERIORATION VIA ACOUSTIC RESPONSE TO GAS FLOW, PRESSURE AND IMPACT

(75) Inventors: Ronald T. Harrold, Murrysville, PA (US); Zal N. Sanjana, Mt. Lebanon, PA (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 648 days.

(21) Appl. No.: 10/262,332

(22) Filed: Oct. 1, 2002

(65) Prior Publication Data

US 2003/0126928 A1 Jul. 10, 2003

Related U.S. Application Data

(60) Provisional application No. 60/326,477, filed on Oct. 1, 2001.

(51) Int. Cl.
*G01N 29/00* (2006.01)

(52) U.S. Cl. .............................. 73/593; 73/602; 73/660
(58) Field of Classification Search ................. 73/593, 73/602, 660, 587, 598, 599, 600, 645; 600/602, 600/660

See application file for complete search history.

(56) References Cited

U.S. PATENT DOCUMENTS

| 4,244,441 | A |   | 1/1981  | Tolman |
| 4,545,250 | A |   | 10/1985 | Miwa |
| 4,619,143 | A |   | 10/1986 | Franken |
| 4,696,191 | A |   | 9/1987  | Claytor et al. |
| 5,152,172 | A | * | 10/1992 | Leon et al. .................... 73/579 |
| 5,195,046 | A | * | 3/1993  | Gerardi et al. ................. 702/35 |
| 5,349,443 | A |   | 9/1994  | Guerra |
| 5,445,027 | A | * | 8/1995  | Zorner ......................... 73/593 |
| 5,670,879 | A | * | 9/1997  | Zombo et al. ............... 324/227 |
| 5,894,092 | A |   | 4/1999  | Lindgren et al. |
| 5,942,690 | A | * | 8/1999  | Shvetsky ....................... 73/660 |
| 6,487,909 | B1 | * | 12/2002 | Harrold et al. ................ 73/593 |
| 6,629,463 | B1 | * | 10/2003 | Naudet et al. ................. 73/579 |

OTHER PUBLICATIONS

US 2003/0056595, Acoustic monitoring of foreign objects in combustionturbines operation, Mar. 27, 2003.*

* cited by examiner

*Primary Examiner*—Hezron Williams
*Assistant Examiner*—Jacques M. Saint-Surin

(57) ABSTRACT

A method of monitoring the condition of a thermal barrier coating on a turbine blade or vane during operation of the turbine is provided. The method includes providing a means for receiving acoustic output of the blade or vane during operation of the turbine and monitoring the acoustic output over time, to determine the condition of the thermal barrier coating on the blade or vane. The acoustic output arises from a force on the blade or vane, such as that due to impact of particles, a pulse of gas pressure or constant gas flow. An apparatus employing the above method for monitoring the condition of the thermal barrier coating during operation of the turbine, is also provided.

15 Claims, 4 Drawing Sheets

PROOF OF CONCEPT TEST: ACTIVE MODE TBC CONDITION DETECTION

HAYNES (R) 230 R ALLOY BARE METAL PLATE

APS TBC PLATE

AWG BONDED TO EDGES LAUNCH SLOW MOVING LAMB OR SURFACE WAVES (1900 M/SEC) INTO PLATES

DIFFERENCES BETWEEN ACOUSTIC SIGNALS RECEIVED VIA ACOUSTIC WAVEGUIDE DUE TO IMPACT OF THERMAL BARRIER COATED AND BARE METAL HAYNES (R) 230 R ALLOY PLATES

DIFFERENCES BETWEEN ACOUSTIC SIGNALS RECEIVED VIA ACOUSTIC WAVEGUIDE DUE TO CONSTANT GAS FLOW OF THERMAL BARRIER COATED AND BARE METAL HAYNES (R) 230 R ALLOY PLATES

MONITORING THERMAL BARRIER COATING DETERIORATION VIA ACOUSTIC RESPONSE TO GAS FLOW, PRESSURE AND IMPACT

CROSS-REFERENCE TO RELATED APPLICATIONS

This application claims priority under 35 U.S.C. § 119(e) to provisional application Serial No. 60/326,477, filed Oct. 1, 2001, and under 35 U.S.C. § 120 to application Ser. No. 09/965,715, filed Sep. 27, 2001, now U.S. Pat. No. 6,668,655 and to application Ser. No. 09/776,818, filed Feb. 5, 2001, now U.S. Pat. No. 6,487,909.

FIELD OF THE INVENTION

The present invention relates to monitoring of combustion turbines for deterioration of the thermal barrier coating on turbine blades and vanes. More specifically, turbine blades and vanes can be monitored for changes in acoustic output, to detect deterioration in the thermal barrier coating.

BACKGROUND INFORMATION

The blades and vanes of gas turbine machines operate in an extremely harsh environment with high gas pressures and velocities and temperatures around 1300° C. In order to withstand this environment, the blades and vanes in a combustion turbine are made of high temperature alloys such as nickel-cobalt, are coated with a thermal barrier coating (TBC) such as yttria-zirconia, and, if necessary, are internally cooled to help dissipate heat. The condition of the TBC is critical because spalling, whereby areas of the TBC flake off or separate from the underlying alloy, can lead to vane or blade failure within hours. At present, machines are shut down at regular intervals and inspected, and damaged blades and vanes are then replaced. Condition monitoring of vanes and blades of operating machines until now has not been available, although gas monitoring has been proposed to look for particulates from the thermal barrier coating as an early warning system.

Typically, gas turbine machines have three or four rows of vanes and blades having thermal barrier coatings and are subjected to the most severe conditions. There may be, depending upon the type of machine, about 50 to 100 blades and vanes per row, and up to approximately 200 to 500 total blades and vanes having a TBC. Currently, it is necessary to periodically stop the turbine and inspect all of these components for deterioration of the coating or other defects. It would be desirable to determine the condition of the thermal barrier coating of these components while a gas turbine machine is in operation. Avoiding the need to periodically stop the turbine for inspection reduces downtime and increases turbine efficiency. Similarly, early detection of defects reduces repair costs and outage time, again increasing turbine efficiency. A need exists for monitoring the condition of the thermal barrier coating of blades and vanes within the turbine over time, while the turbine is in operation, to detect changes in the coating and deterioration thereof.

Various methods and systems for detecting and locating defects within a turbine engine or in turbine components have been proposed. Previous work of the current inventors, pending U.S. application Ser. Nos. 09/965,715 and 09/776,818, and expressly incorporated herein by reference, has shown that acoustic monitoring of a combustion turbine can be used to detect the presence of foreign objects in the turbine and to detect wear in the TBC by generating acoustic signals and receiving the signals with an acoustic sensor. As the coating deteriorates, the magnitude and velocity of the acoustic waves changes, indicating the need for service in the turbine.

U.S. Pat. No. 5,445,027 describes a method and apparatus for detecting and locating defects (such as cracks) in a component of a turbine. The method involves using a probe in the interior of the turbine to measure the acoustic spectrum of the turbine, which is then compared with a reference spectrum. Deviations from the reference indicate a damaged blade.

There continues to be a need for methods and apparatus for detecting the deterioration of the thermal barrier coating on blades and vanes in a combustion turbine, to provide an indication of when a turbine needs to be shut down for maintenance.

SUMMARY OF THE INVENTION

Accordingly, the present invention provides a method of monitoring the condition of the thermal barrier coating of a turbine blade or vane by providing a means for receiving acoustic output of the blade or vane during operation of the turbine and monitoring this acoustic output over time, to detect deterioration of the thermal barrier coating on the blade or vane. An acoustic waveguide is bonded to a suitable location within the combustion turbine, typically to a vane. Where the acoustic waveguide exits the turbine, an acoustic sensor such as a piezoceramic crystal is attached, for conversion of the acoustic signal to an electrical signal. The electrical signal can then be displayed through a visual means, such as an oscilloscope, or stored for later analysis.

The acoustic output arises from a force applied by the working gas or its constituents on the blade or vane, for example, such force being due to the impact of a foreign object or particle within the turbine, a pulse of gas pressure, or constant gas pressure over time.

For example, it has been found that the acoustic signal generated by the impact of an object on metal parts having a thermal barrier coating differs from that of uncoated metal parts, and thus a comparison of the acoustic signal generated by foreign objects inside the combustion turbine with new blades and vanes can be compared to the acoustic signal generated at a point later in time, when the parts have experienced service and have been exposed to the harsh conditions of the turbine, to indicate whether the thermal barrier coating has deteriorated.

It is an object of the present invention, therefore, to detect changes in the thermal barrier coating of combustion turbine blades and vanes while the turbine is in operation.

It is an additional object of the present invention to use acoustic monitoring of signals generated within the turbine during operation to detect changes in the thermal barrier coating over time.

It is an additional object of the present invention to compare acoustic signals generated while the turbine is in operation over time, to detect changes in the thermal barrier coating of the turbine parts.

These and other aspects of the present invention will become more readily apparent from the following description, figures and appended claims.

BRIEF DESCRIPTION OF THE DRAWINGS

The invention is further illustrated by the following drawings in which.

DETAILED DESCRIPTION OF PREFERRED EMBODIMENTS

Figure 1:
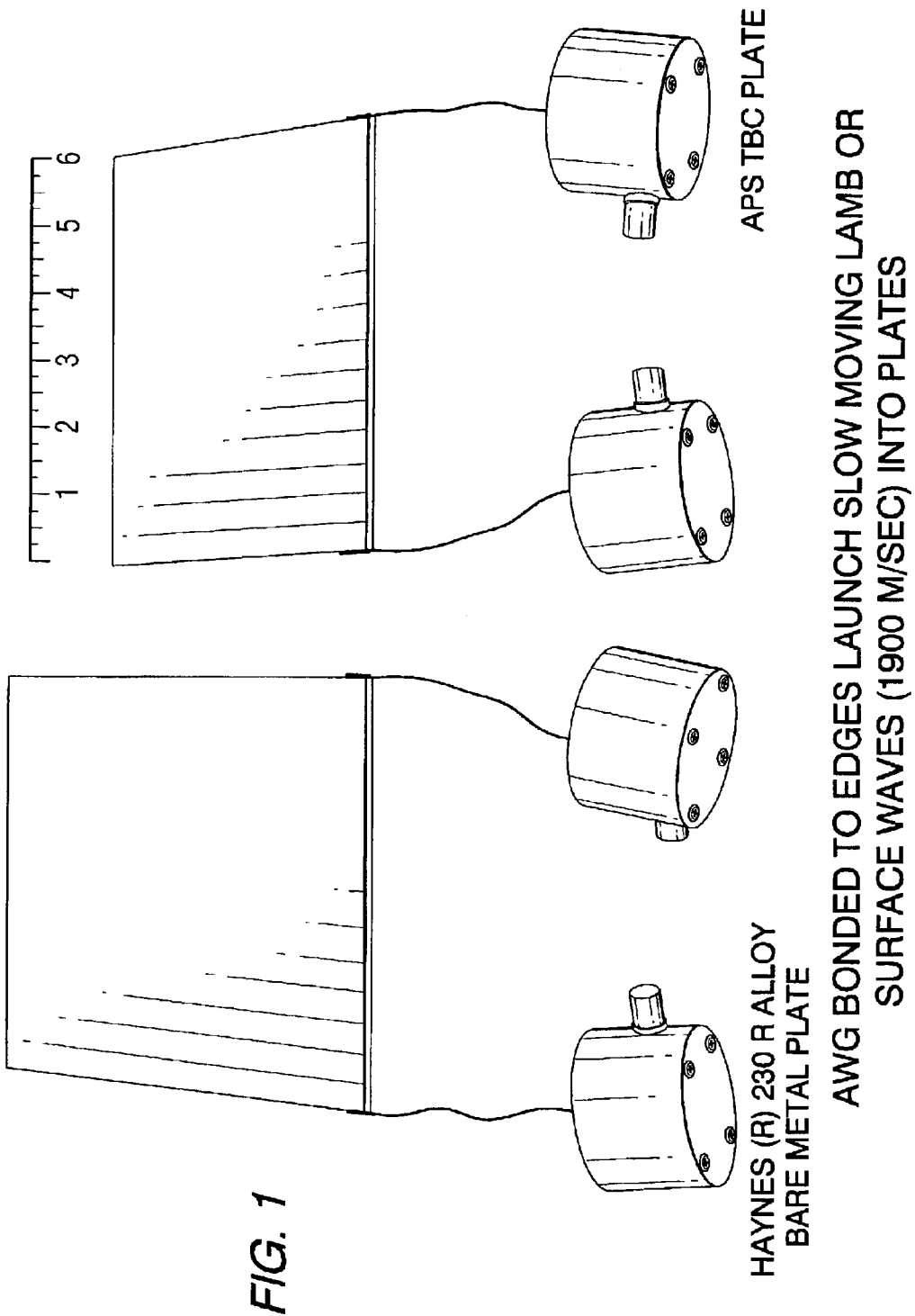
FIG. 1 shows an acoustic waveguide bonded to the edges of uncoated and coated metal plates.

Acoustic experimental work with both uncoated metal (Haynes (R) 230 R alloys) and metal with an air plasma sprayed thermal barrier coating (TBC), has shown some large characteristic differences between them. For example, with a very modest impact of a foreign object, the acoustic response from metal having a TBC is ten times less than the response of uncoated metal. Similarly, the TBC dampens the acoustic signal of a pulsed gas jet to half the time of that for uncoated metal, and a constant gas flow yields three times the signal level from the thermal barrier coated metal as compared with uncoated metal. These characteristics can be used to help monitor the deterioration of TBC on vanes and blades of gas turbine machines in operation.

The present invention provides a method of monitoring the condition of a thermal barrier coating on a turbine blade or vane, while the turbine is in operation. The method comprises providing a means for receiving acoustic output from blades and vanes during operation of the turbine, the acoustic output arising from a force applied by the working gas or its constituents on the blades or vanes within the turbine. A preferred acoustic output, for monitoring purposes, are surface waves produced by various forces within the turbine. This acoustic output is then compared with the acoustic output data gathered earlier in time, when the blades and vanes of the turbine are new. Preferably, the magnitude of surface waves is monitored over time, with changes in the acoustic output over time (changes in the magnitude of surface waves) indicating deterioration of the thermal barrier coating on blades or vanes within the turbine.

The force arises from the working gas or its constituents, including, but not limited to, the impact of foreign objects, pulsed gas pressure or the impact of constant gas pressure on the blades or vanes within the turbine. For example, as each blade passes a vane, the blade will produce a gas pressure pulse and resulting acoustic wave at that vane. Constant gas flow across vanes also produces an acoustic signal, as does the impact of a foreign object on a blade or vane. The foreign object is a ceramic or metal particle from chipped coatings or metal parts. Additionally, non-damaging particles can be introduced into the gas stream, via fuel injection nozzles or steam injection parts, if available. Suitable particles include about 0.5 mm diameter Pyrex glass beads or soft ceramics materials, which will momentarily survive the high temperature environment, but will disintegrate upon impact with the thermal barrier coatings and not cause damage. However, an acoustic shock wave would result. The acoustic output of the impact of these particles on vanes or blades can be monitored, as above, to detect changes in the TBC over time.

Typically, the means for receiving the acoustic output while the turbine is in operation will comprise an acoustic waveguide bonded to a location inside the turbine, preferably a vane, although it can also be bonded to the bearing housing for monitoring the acoustic output from the rotating blades. A special feature of acoustic waveguides is that they can be bonded to vanes by either a point or direct contact or by bonding a few inches of acoustic waveguide length to the vane edges. It has been found that by bonding a short segment (a few inches, or at least one wavelength or more) of an acoustic waveguide to vane edges, surface waves can be received. If the acoustic waveguide is bonded by direct or point contact, only longitudinal waves are received. With the acoustic waveguides bonded for a wavelength or more (based on longitudinal wave velocity in waveguide material), the surface waves in the surface to be monitored are converted to longitudinal waves travelling within the waveguide. The preferred listening or received mode measurement is the magnitude of the transmitted surface wave. Bonding lengths of one wavelength vary from approximately 1 to 5 inches. Previous methods dealing with acoustic surface waves use conventional wedge/critical angle techniques to convert longitudinal (Bulk) waves from an ultrasonic transducer into surface waves travelling at different depths within the surface to be monitored. In addition, these methods emphasize velocity and frequency measurements for finding defects at different depths. In contrast, the surface wave technique of the present invention uses the magnitude of the received acoustic surface wave which has been found to be very sensitive (10 to 1) to surface conditions, such as spalling of a thermal barrier coating.

After the acoustic waveguide exits the turbine, it is bonded to an acoustic receiver such as a piezoceramic crystal, preferably one that can receive acoustic signals in the ultrasonic region and is resonant around 80 kHz, to convert the acoustic signal to an electrical signal for further study or storage. The acoustic signal can be filtered to remove background turbine noise; typically this background noise will be the portion of the signal below 30 kHz.

Acoustic waveguides (AWG) are typically small diameter wires or rods (0.010 inch to 0.250 inch) which can be made from a variety of materials. Their function, in the present invention, is to transmit an acoustic signal from within the harsh operating environment of the turbine to a transducer located outside the turbine, for measurement and analysis, to analyze changes in acoustic signals within the engine. The AWG may also be used to transmit acoustic signals to the turbine from a transducer located outside the engine.

In order to accomplish this function, the AWG must be a good transmitter of high frequency (20–500 kHz) acoustic signals. This property is typically found in hard materials with a low Poisson's Ratio (ratio of change in diameter to change in length for a wire or a rod under tension). A variety of metals (platinum and its alloys, tungsten and its alloys, stainless steels, nickel and cobalt based alloys), non-metals (alumina fibers, quartz, sapphire) and fiberglass or carbon (graphite) reinforced polymer composites meet this requirement.

The use of an AWG within a combustion turbine imposes additional severe restraints on the choice of an AWG material. The AWG must be able to survive several years in the turbine environment of hot, oxidative gases at temperatures up to 1500° C., high pressures up to 400 psi and a variety of dynamic stresses created by the gas flow and vibration. The AWG must be weldable to the nickel and cobalt-based alloys commonly used in turbine parts and the welds must survive for several years. These conditions rule out the use of composite materials (which cannot withstand such high temperatures), and the use of non-metallics (which cannot be attached to the vanes at operating temperatures). Tungsten and its alloys cannot be used because they will not survive in a hot oxidative environment. It has been found that a 1-mm platinum or 1-mm platinum/13% rhodium wire provides an optimum choice for the material of the AWG, and allows monitoring critical turbine components in real-time while the turbine is in operation.

The acoustic signals generated while the turbine is in operation are then compared to the acoustic signals measured at different points in time, to detect any changes over time. Specifically, the magnitude of received acoustic surface waves is compared to the magnitude of acoustic surface waves received at other points in time. Any means for comparison can be used, such as visual comparison, comparison by Fourier analysis, correlation analysis or other methods known in art for analyzing changes in data over time. As described above, it has been found that acoustic output from uncoated metal parts differs from that of coated parts: the thermal barrier coating provides a significant damping effect on acoustic signals arising from the impact of metal objects and gas pressure on the metal part, while the acoustic output from constant gas flow is increased on the TBC part, as compared with uncoated metal. As the thermal barrier coating deteriorates, the acoustic signals will change, indicating a need for maintenance of the turbine.

As will be appreciated by one skilled in the art, the acoustic signals generated while the turbine is in operation wil be a combination of signals produced by the impact of particles and gas flow. The combined signals will change over time, with the deterioration of the coating, and thus a comparison of the combined signals generated at different points in time can indicate the need for service on the turbine.

In an additional aspect of the present invention, an apparatus for monitoring the condition of a thermal barrier coating on turbine blades or vanes is provided. The apparatus comprises a means for receiving the acoustic output of blades or vanes during operation of the turbine, and a means for monitoring this acoustic output over time, to detect deterioration of the thermal barrier coating on the blades or vanes during operation of the turbine; the acoustic output arises from a force applied by working gas or its constituents on the blades or vanes.

The force arises from the impact of a foreign object, pulsed gas pressure or the impact of constant gas pressure on said blade or said vane.

As described above, the means for receiving a first acoustic output is an acoustic waveguide as described above, bonded to a location inside the turbine, preferably a vane or bearing housing. After the acoustic waveguide exits the turbine it is bonded to an acoustic receiver such as a piezoceramic crystal, preferably one that can receive acoustic signals in the ultrasonic region and is resonant around 80 kHz, to convert the acoustic signal to an electrical signal for further study or storage. The acoustic signal can be filtered to remove background turbine noise; typically this background noise will be the portion of the signal below 30 kHz.

EXAMPLES

The following examples are intended to illustrate the invention and should not be construed as limiting the invention in any way.

The following measurements were made, using Haynes (R) 230 R alloy metal plates, one with an air plasma sprayed TBC and one with uncoated metal, and both having attached acoustic waveguide sensors (FIG. 1). The tests were conducted in the listening mode in which the attached AWG and piezoceramic sensors received acoustic signals for oscilloscopic display:

Example 1

Impact

A one gram steel ball was dropped from a height of 10 cm onto the surface of each plate. Other distances, compositions and masses can also be used.

Figure 2A:
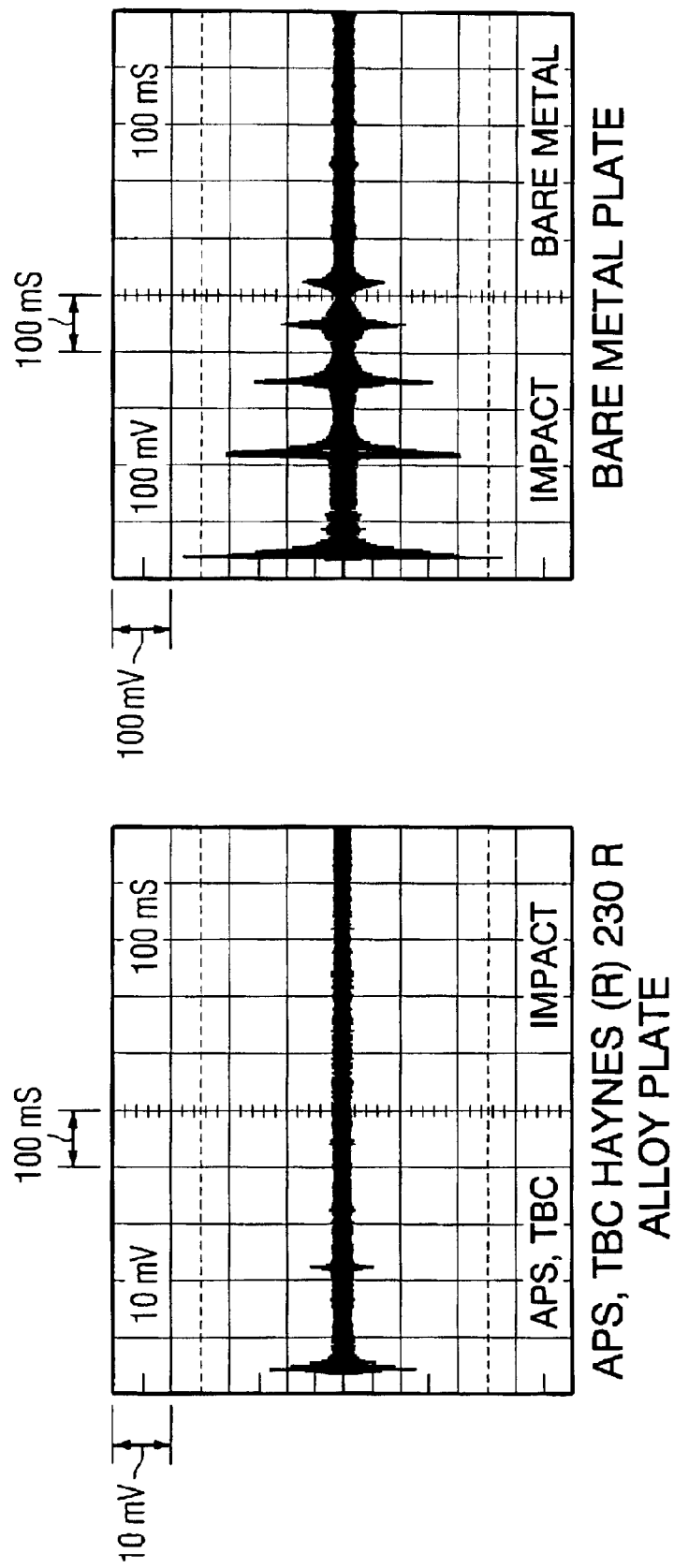
FIG. 2 illustrates the differences between acoustic signals received via acoustic waveguide due to impact, gas pulse and constant gas flow for thermal barrier coated and uncoated metal Haynes (R) 230 R alloy plates.

The results are shown in FIG. 2A. It can be seen that the TBC plate had a first impact magnitude of 12 mV, with just one bounce recorded. With the uncoated metal plate, the first impact yielded a 270 mV signal and recorded four bounce signals. Clearly, use of a TBC results in over ten to one damping of impact signals.

Example 2

Gas Pulse

An 8 psi, 0.2 sec gas pulse originating 5 cm above the plate was directed at each plate. Other pressures, durations and distances may be used, i.e. about 2–20 psi, about 0.1–0.3 sec, and about 1–10 cm, respectively, would be appropriate.

Figure 2B:
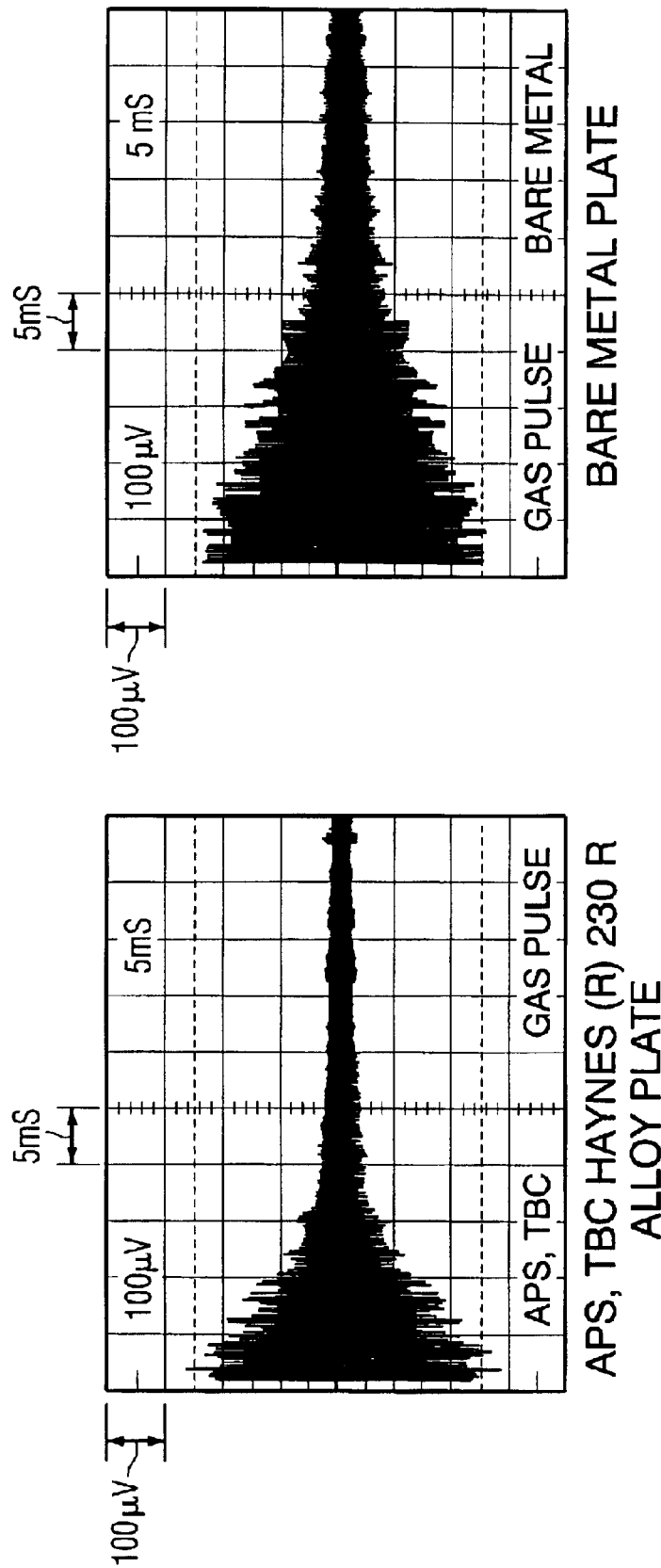

FIG. 2B shows the results of the gas pulse tests. It can be seen that both plates yielded similar signal levels, but the signal on uncoated metal lasted for 30 msec, whereas the signal from the TBC plate was damped out in 15 msecs.

Example 3

Constant Gas Flow

A 6 psi, constant gas flow originating 5 cm above plate was directed at each plate. The pressure and distances could vary, ranging from about 2–20 psi and about 1–10 cm would be appropriate.

Figure 2C:
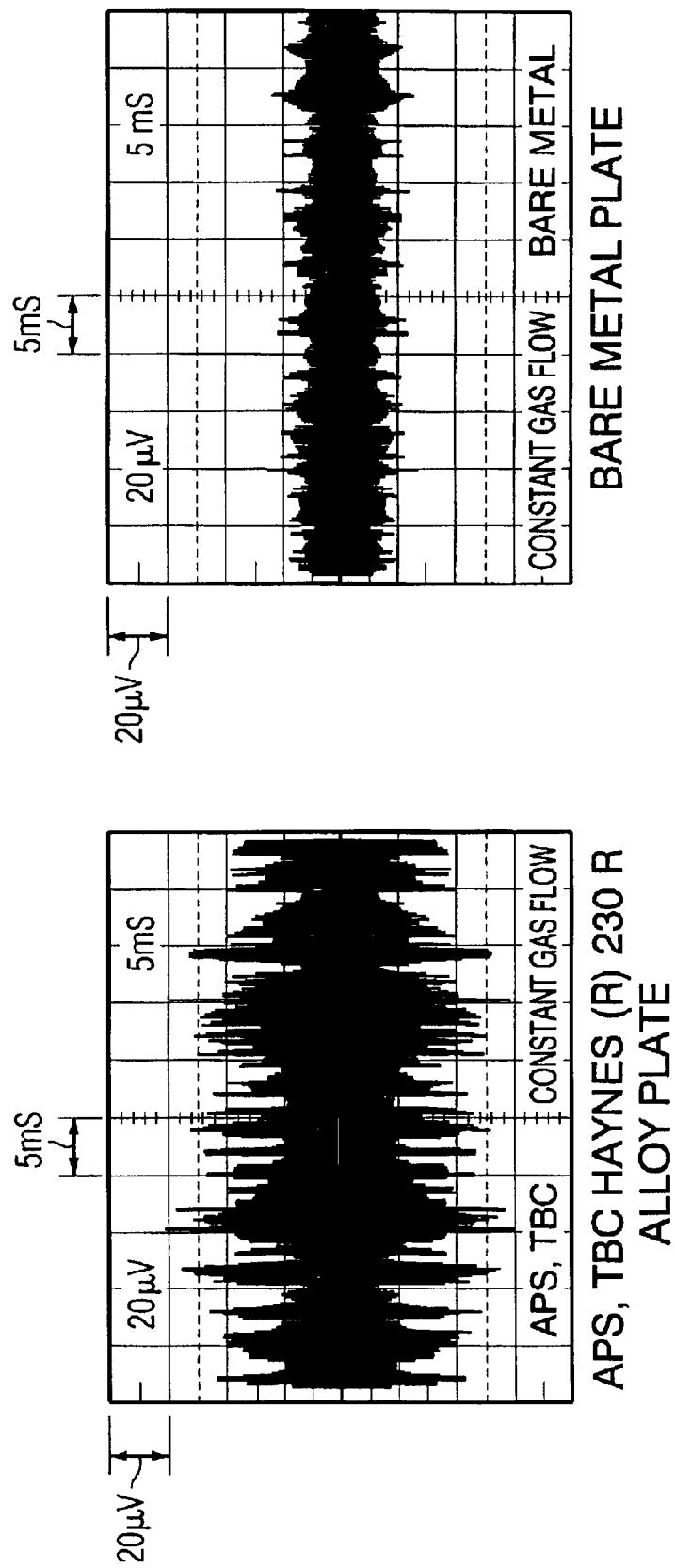

In these tests, FIG. 2C, the uncoated metal plate yielded only a 20 µV signal, while the signal from the APS, TBC plate was three times higher, or 60 µV. It appears that the coarse (having surface irregularities) TBC breaks up the air flow and yields a higher signal level.

The acoustic characteristics described in Examples 1, 2 and 3 can be used with AWG sensors to monitor the deterioration of TBC on the vanes and blades of operating gas turbine machines.

Whereas particular embodiments of this invention have been described above for purposes of illustration, it will be evident to those skilled in the art that numerous variations of the details of the present invention may be made without departing from the invention as defined in the appending claims.

What is claimed is:

1. A method of monitoring the condition of a thermal barrier coating on a turbine blade or vane in a combustion turbine comprising:

providing a means for receiving acoustic output of said blade or said vane during operation of said turbine; and monitoring the magnitude of surface waves of said acoustic output over time to detect deterioration of said thermal barrier coating on said blade or said vane;

said acoustic output arising from a force applied by working gas or its constituents on said blade or said vane.

2. The method of claim 1, wherein said means for receiving said acoustic output is a short segment of an acoustic waveguide bonded to a surface of said vane.

3. The method of claim 2, further comprising a means for converting said acoustic output to an electrical signal.

4. The method of claim 3, wherein said means for converting said acoustic output to an electrical signal is a piezoceramic crystal.

5. The method of claim 1, further comprising the step of filtering said acoustic signal to remove a portion of said acoustic signal below 30 kHz.

6. An apparatus for monitoring the condition of a thermal barrier coating on a turbine blade or vane in a combustion turbine comprising:

means for receiving acoustic output of said blade or said vane during operation of said turbine; and means for monitoring the magnitude of surface waves of said acoustic output over time to detect deterioration of said thermal barrier coating on said blade or said vane during operation of said turbine;

said acoustic output arising from a force applied by working gas or its constituents on said blade or said vane.

7. The apparatus of claim 6, wherein said means for receiving said acoustic output is a short segment of an acoustic waveguide bonded to a surface of said vane.

8. The apparatus of claim 6, further comprising a means for converting said acoustic output to an electrical signal.

9. The method of claim 8, wherein said means for converting said acoustic output to an electrical signal is a piezoceramic crystal.

10. The apparatus of claim 6, further comprising a means for filtering said acoustic signal to remove a portion of said acoustic signal below 30 kHz.

11. A method of monitoring the condition of a thermal barrier coating on a turbine blade or vane in a combustion turbine comprising:

introducing non-damaging particles into a gas stream of said turbine;

providing a means for receiving acoustic output of said blade or said vane, said acoustic output arising from impact of said non-damaging particles on said blade or vane during operation of said turbine; and monitoring the magnitude of surface waves of said acoustic output over time to detect deterioration of said thermal barrier coating on said blade or said vane.

12. The method of claim 11, wherein said means for receiving said acoustic output is a short segment of an acoustic waveguide bonded to a surface of said vane.

13. The method of claim 12, further comprising a means for converting said acoustic output to an electrical signal.

14. The method of claim 13, wherein said means for converting said acoustic output to an electrical signal is a piezoceramic crystal.

15. The method of claim 11, further comprising the step of filtering said acoustic signal to remove a portion of said acoustic signal below 30 kHz.

* * * * *